United States Patent [19]

Hennessy et al.

[11] Patent Number: 4,729,876
[45] Date of Patent: Mar. 8, 1988

[54] BLOOD ANALYSIS SYSTEM

[75] Inventors: James W. Hennessy, Trumbull; Henry R. Angel, Fairfield; William J. Casey, Jr., Milford; Samuel P. Baron, Fairfield, all of Conn.

[73] Assignee: Nova Celltrak, Inc., Trumbull, Conn.

[21] Appl. No.: 931,894

[22] Filed: Nov. 17, 1986

Related U.S. Application Data

[63] Continuation of Ser. No. 675,378, Nov. 27, 1984, abandoned.

[51] Int. Cl.$^4$ .............................................. B01L 11/00
[52] U.S. Cl. .................................. 422/103; 73/863.73; 422/63; 422/100
[58] Field of Search ................. 422/63, 100, 101, 103, 422/71; 436/180; 137/625.45; 73/864.81, 864.82, 864.83, 863.73

[56] References Cited

U.S. PATENT DOCUMENTS

| | | | |
|---|---|---|---|
| 2,973,117 | 2/1961 | Conklin | 73/863.73 |
| 3,080,759 | 3/1963 | McQuaid | 73/863.73 |
| 3,404,780 | 10/1968 | Jungner | 422/63 |
| 3,752,167 | 8/1973 | Makabe | 137/625.46 |
| 3,858,450 | 1/1975 | Jones | 422/100 |
| 3,964,513 | 6/1976 | Molner | 73/864.83 |
| 3,990,853 | 11/1976 | Godin | 422/103 |
| 3,991,055 | 11/1976 | Godin et al. | 436/100 |
| 4,125,375 | 11/1978 | Hunter | 210/221.1 |
| 4,152,391 | 5/1979 | Cabrera | 422/103 |
| 4,220,621 | 9/1980 | Simpson et al. | 422/103 |
| 4,310,022 | 1/1982 | Cohen | 137/625.46 |
| 4,501,297 | 2/1985 | Baker | 137/625.46 |
| 4,517,302 | 5/1985 | Saros | 436/180 |

FOREIGN PATENT DOCUMENTS 855234  11/1960  United Kingdom ............. 73/864.83

Primary Examiner—Michael S. Marcus
Attorney, Agent, or Firm—Dann, Dorfman, Herrell and Skillman

[57] ABSTRACT

A blood analyzer is provided with means to automatically pierce the sealed closure of a vacuum container or to aspirate through an aspirator tip blood samples to be analyzed. The samples are drawn serially through a repositionable valve structure, preferably of rotary form, and having three members in layers with aligned ports in one position to receive the blood that is drawn through the valve by a syringe type aspirator. Another position of the valve connects diluent supplies providing measured amounts of diluent to wash out the bores of the middle member of the valve containing amounts of blood measured by the size of the bores. In the case of the red blood cell measurement, where the bore is extremely small, a larger by-pass port is provided in parallel with the sample containing bore to allow more rapid flow simultaneously through both.

Blood analysis is performed by separate conventional cell counter arrangements for each of the red and white counts. A novel configuration involves a bore through a block generally tangential to a bore which engages a cylindrical chamber in the sidewall of which is a jewel orifice. A foil electrode is used in the tangential passage and a larger tapered electrode with the smaller end near the orifice in the cylindrical output chamber. A discontinuity in the form of an air bubble in a passage feeding the counter apparatus enables the position of the bubble to be sensed at one place to turn on the counter and in another place in the passage to turn off the counter.

The three-layer valve structure has various special indexing features and cleaning features, and the intake devices have features associated with cleaning as well.

7 Claims, 18 Drawing Figures

BLOOD ANALYSIS SYSTEM

RELATED U.S. APPLICATION DATA

This application is a continuation of U.S. Ser. No. 675,378, filed Nov. 27, 1984 now abandoned.

The present invention relates to a system for automatically analyzing blood. This hemotology system is capable of quantitative determination of the following: a white blood cell count (WBC); a red blood cell count (RBC); hemoglobin (HGB); mean corpuscular volume (MCV); platelet count (PLT); and mean platelet volume (MPV). The system is also projected to be capable of caculating from test results of the RBC, HGB, MCV, PLT and MPV the following: hematocrit (HCT); mean corpuscular hemoglobin (MCH); mean corpuscular hemoglobin concentration (MCHC); and thrombocrit (TCT).

More specifically, the present invention has improvements in the overall system and in such specific features as a device for receiving a container of blood.

THE PRESENT STATE OF THE ART

The present state of the art usually involves a certain amount of manual handling of blood samples although a limited amount of automatic handling features have been developed. Present processing normally involves sequential dilutions and usually sequential tests first on red blood count then on white blood count. Even the best current process usually involves a relatively long time in processing samples and obtaining full results.

The equipment that is available is also difficult to use and frequently difficult to clean and maintain. Failure to maintain the parts sufficiently clean frequently results in the sticking together of relatively movable parts, and/or the clogging of small tubes and apertures. Thus, the cleaning and maintenance job is further increased where cleaning and maintenance has not been done regularly and soon after use, particularly in a situation where blood or blood mixtures have gotten between contacting relatively movable parts.

THE PRESENT INVENTION

The preferred form of hematology system of the present invention incorporates an internal diluting system which automatically and simultaneously makes two dilutions and sends both dilutions to the analyzer. Blood samples are automatically removed either from open containers or vacuum sealed containers and automatically processed for analysis thereafter. The throughput of the system is approximately 60 specimens per hour. Although beyond the scope of the present invention disclosure, the displays and indicators on the screen output will provide the operator with information concerning the status of every test and will prompt to alert the operator to troubleshoot problems such as clogs and overrange. The modular construction makes for easy servicing.

Three methods of specimen introduction are employed. Use of vacutainers minimizes whole blood handling therefore reducing the risk of hepatitis. Alternatively, a whole blood aspirate tip draws the blood to be automatically diluted and sent to the analyzer for measurement. The most conventional is manual predilute in which the operator makes the first microsample. The instrument may be then used to prepare the second dilution. The dilutions are poured into the instrument manually.

More specifically, the present invention is directed to various components of structure and various aspects of a fluid system employed with those components.

At the heart of the system is a stacked three layer valve structure, preferably rotary in form employing flat ceramic cylinders or discs with ultra flat opposing faces. In various embodiments of whatever form the middle member moves relative to the outer members, and that movement can be linear, or nonrotational. In the preferred rotation form, the middle disc is rotatable about a fixed center spindle relative to the outer two discs which are held fixed relative to the housing. The middle member has at least two positions of operation, and preferably at least three positions of operation, such that a port through the middle member is aligned with ports in the outer two in each of said at least two index positions. The position of the middle member relative to the other members is preferably sensed by sensor means which controls the positioning and indexing of the middle member by a motor drive.

Various aspects of the movable valve member, whether rotary or otherwise are novel. One of the more interesting of these is the cleaning arrangement which is provided by keeping the spacing between the separated members very small but sufficient to allow interposing jets of cleaning fluid between them. The cleaning fluid is drawn across the opposed faces and spreads over the entire surface as it is drawn by vacuum. In the rotary valve configuration, a vacuum effect is distributed around the periphery of the disc by a circular gutter channel outside of all of the ports. Cleaning fluid issues from jets through the hollow spindle about which rotation takes place. Such an arrangement causes the cleaning fluid to spread 360 degrees over both of the surfaces as it is drawn to the gutter channel to be evacuated.

Another aspect of the three layer sliding valve arrangement is that a very small precision blood sample can be subtended within a very small diameter precise volume bore through the middle member. Such a small sample is needed for the red blood count analysis. A larger bore diameter, but still precise volume, is used for the sample of the white blood count and mixed with less diluent. In accordance with the present invention, the movable member is moved from the sample obtaining position to another location indexed with the outer members in which diluent is fed through the fixed volume bores to wash them out. In the case of the red blood sample, a parallel channel is provided to enable the much greater amount of diluent to by-pass the ultra small sample bore. Thus, the greater precise measured amount of diluent can be fed through the parallel ports at the same time another precise measured amount of diluent is fed through the larger bore.

Other features of the present invention relate to such novel structures, for example, as the device for receiving a container of blood closed by a resilient self-sealing closure and enabling automatic removal of blood therefrom. Such device includes a penetrating tubular member (a hypodermic needle) fixedly supported on the frame and having an end designed to penetrate the resilient closure of such a container of blood. It is connected to blood evacuation means to enable blood to be withdrawn from the container. The device also includes guide means supported relative to the frame for receiving the container in predetermined orientation such that its closure is directed toward said tubular means. Movable support means in alignment with the guide means is supported on and guided by the frame for reciprocating motion toward and away from the tubular means parallel to the axis of the tubular means. The movable support means enables the container inserted into the guide with its resilient closure end first to be pushed inward against the movable support to allow penetration of the resilient closure by the tubular means. Such penetration of the closure enables blood to be drawn out from the container through the tubular member.

Various features in connection with the device enable cleaning by pumping cleaning fluid through the needle and evacuation of the cup member through a drain tube which extends through the bottom the cup and is connected with vacuum means to withdraw the fluid.

Another features of the invention is an aspirator tip device for drawing blood out of an open container. The aspirator tip consists of a hollow tube supported on the frame. Suitable supply line means is connected to the aspirator tip enabling withdrawal of fluid from the aspirator tip. Movable cover means is supported on the frame in position to be moved out of the way to enable the container to be placed under the aspirator tip. The movable cover means is spring urged to return to a position covering the aspirator. The cover also provides closure means surrounding the tip of the aspirator and having a drain and fluid connection means to remove fluid for cleaning the aspirator tip passed through the aspirator tip into the closure.

The invention also relates to a blood analysis equipment in which sensing means is supplied at a point along the line to the cell counter to detect a discontinuity in the sample and at a second point along the line for the same purpose. Means is provided for injecting discontinuity into the sample in the form of an air bubble. Sensors are spaced such that as the air bubble passes the first sensor, the counter will be activated and when the air bubble passes the second sensor, the counter will be deactivated thereby having counted the particles in a predetermined volume equivalent to the that of the line between the sensors.

Another aspect of the present invention is a new process of blood analysis. In this process, a single control valve is positioned in a first position to draw blood from a supply into a measuring bore in the control valve. The valve is repositioned to a second position in which a measured amount of diluent is permitted to flow through and wash out the measuring bore containing the blood sample into a test container. The valve is then moved to a third position and means for recharing the measured diluent supply is activated to replenish those supplies.

Another novel process relates to providing a suitably diluted blood sample and passing it through a tube into a counter. An air bubble is then injected into the tube at the sample to provide a discontinuity between the sample and the air bubble. Detector means is provided along the tube to detect the passage of the air bubble and cause initiation of counting by the counter. Preferably, a second detector is used to detect the discontinuity later down the tube to discontinue the counting.

DESCRIPTION OF A PREFERRED EMBODIMENT OF THE INVENTION

For a better understanding of the present invention, reference is made to the accompanying drawings in which.

Figure 1:
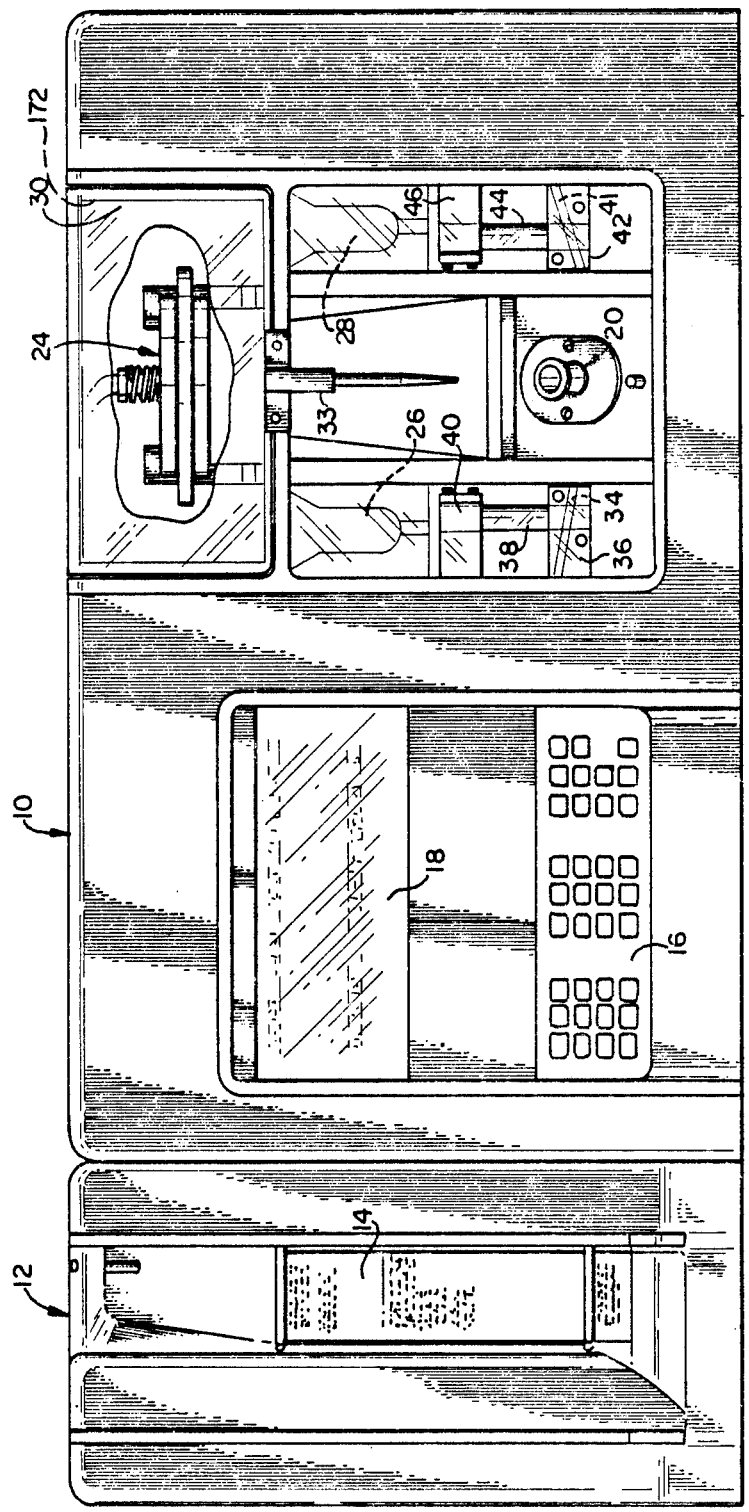
FIG. 1 is an elevational view from the front of a proposed apparatus in accordance with the present invention.

Referring first to FIG. 1, there is illustrated a preferred blood analysis apparatus in accordance with the present invention, housed within two adjacent housings 10 and 12. Housing 10 encloses and supports the mechanical and fluid handling portions of the system as well as input control and display functions. Add on cabinet 12 houses a printer responsive to data generated by the computer within cabinet 10 to print out on slips 14 a hard copy of the blood test results. Input information, such as the nature of a blood test required, is input to the system through keyboard 16 to the internal computer and electronic system. Output of test information is displayed on alpha numeric display 18, and may be printed out on slips 14 if the printer in housing 12 is employed.

Blood samples may be handled automatically either with open or sealed vacuum containers. vacuum containers are inserted into receptacle 20 with their resilient closure down for automatic puncture and removal of blood samples. Samples from open containers are fed into the system through aspirator 22. The system has at its heart a rotary valve 24 which is repositioned for various steps in the automatic handling of the blood sample including a dilution step by which blood properly diluted for a red blood count is placed into container 26. A properly diluted sample for a white blood count is placed in container 28. These containers are open and accessible from above when the hinged transparent cover 30 conforming to the shape of the front and top of the housing is open. Cover 30 rotates about a hinge at its top edge to expose valve 24 for maintenance and repairs. Raising cover 30 also allows hand diluted samples to be added to the containers 26 and 28 from above.

A start switch lever 33 is also provided just below the cover. The start switch is actuated to enable the system to begin its sequence of test steps.

Properly diluted red blood samples are fed by suitable tubular connection from container 26 to the counter portion. The counter container consists of a passage 34 in block 36 generally tangent to a jewel orifice of great precision in the sidewall of vertically oriented tube 38. Tube 38, in turn, is supported by a bracket 40. Similarly, white blood counts are made by passing the diluted and lysed white blood sample from container 28 by suitable tubing connection through passage 140 into block 42 so that it passes tangent to tube 44 whose sidewall contains a jewel orifice of suitably different dimensions. Tube 44 and support block 42 are supported on the housing by bracket 46.

It will be appreciated that internally of the housing 10 there are located a great many necessary electrical and hydraulic system components and lines as well as the computer, counter, processing means, input circuitry, and the like, which are conventional as components, but the combination of which is new. Much of the control means is omitted in this disclosure because the claimed novelty herein pertains primarily to the mechanical and fluid systems of the present invention. The systems necessarily involve a great deal of tubing, valves and other components not displayed to the user but performing very imporant and necessary functions.

Figure 2:
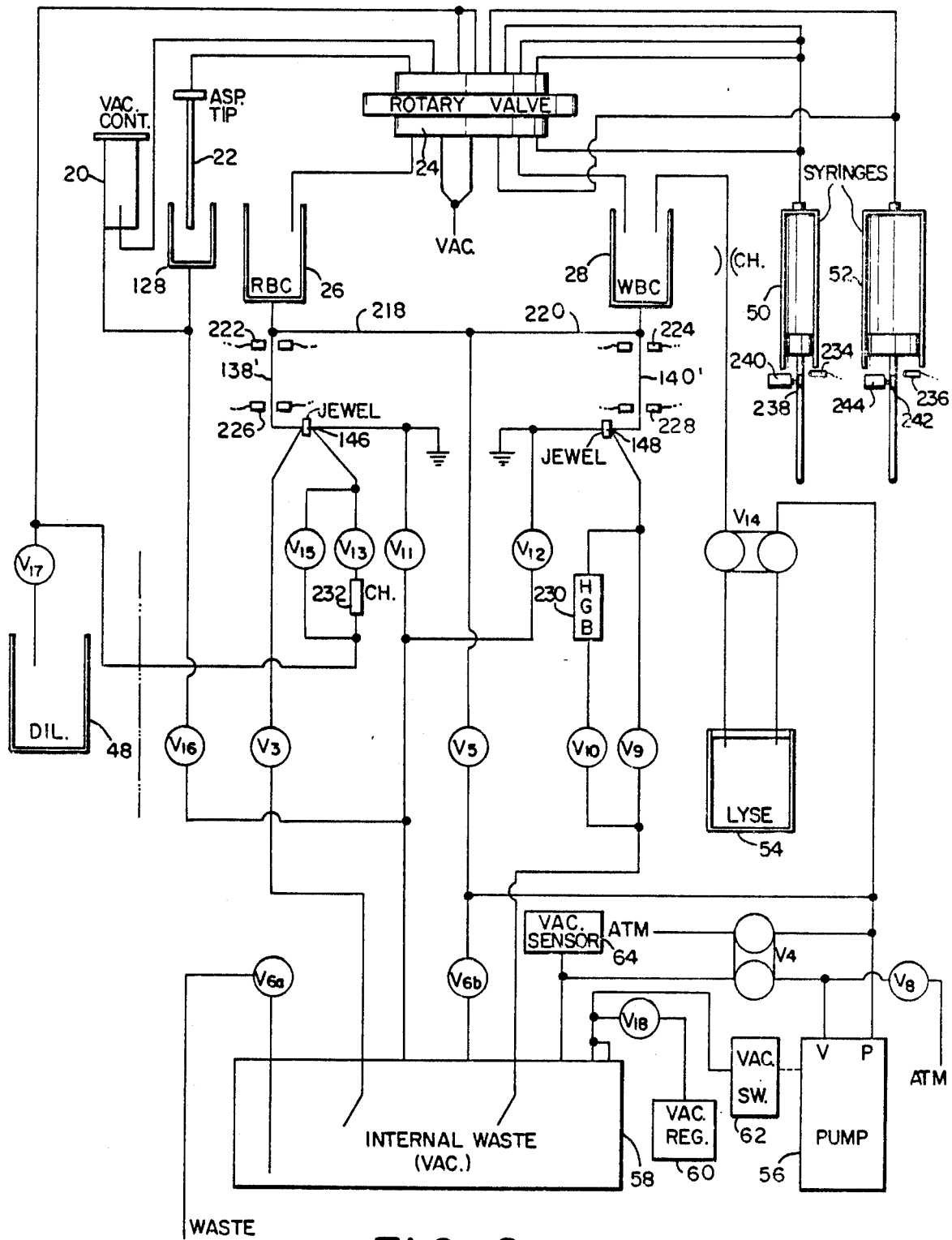
FIG. 2 is a schematic diagram showing the flow and control of fluids through the device.

The principle parts of the fluid system are shown schematically in FIG. 2. FIG. 2 contains components, or parts related to the components already disclosed, as well as such additional components as are needed to complete the fluid system. It will be understood that the single lines shown, are intended to represent tubing or pipe which, in some cases, is flexible. No effort has been made, nor needs to be made, to explain conventional connections between such tubing or pipe and various components.

Input into the system is preferably through the aspirator tip 22 which draws blood from a container which is open, or, from a vacuum container inserted into the vacuum container input structure 20. In either case, input is into a rotary valve 24 whose positioning is determined by what stage of the process is involved. In this connection, it should be noted that the lines shown as input to the rotary valve in FIG. 2 are, indeed, merely input lines and their positioning relative to the valve in this schematic showing is not significant except that they are properly shown at the top or the bottom of the valve. Diluent is supplied from diluent supply 48 through valve 24 for various purposes including the filling of the 10 milliliter and 25 milliliter syringes 50 and 52, respectively. Diluted red blood test samples are collected and mixed in red blood count container 26 and white blood count test samples are collected and mixed in white blood count container 28. Lyse material for the processing of the white blood count is obtained from container 54.

A vacuum pump 56 provides a vacuum for various purposes including to reduce the pressure within internal waste container 58. It will be observed that the vacuum level is sensed by a vacuum sensor 64 which trips some sort of alarm indicator such as a light or buzzer, indicating a problem relating to insufficient vacuum, if the pressure in the vacuum falls to a predetermined level. Blockage or other cause of problem can then be investigated by the operator and corrected. Vacuum switch 62 operates pump 56 to normally maintain vacuum at a desired vacuum level in internal waste tank 58 through normally opened two-sided valve V4. Vacuum regulator 60 is normally connected to the system to help smooth out vacuum levels. Valve V18 to regulator 60 is closed when valves V6a and V6b are opened and V4 is closed to apply pressure to the waste fluid tank 58 to clean it out through valve V6a to waste. At that same time, valve V8 is opened to atmosphere (ATM).

FIG. 2 will be further explained in terms of the operation of the system hereafter.

Figure 3:
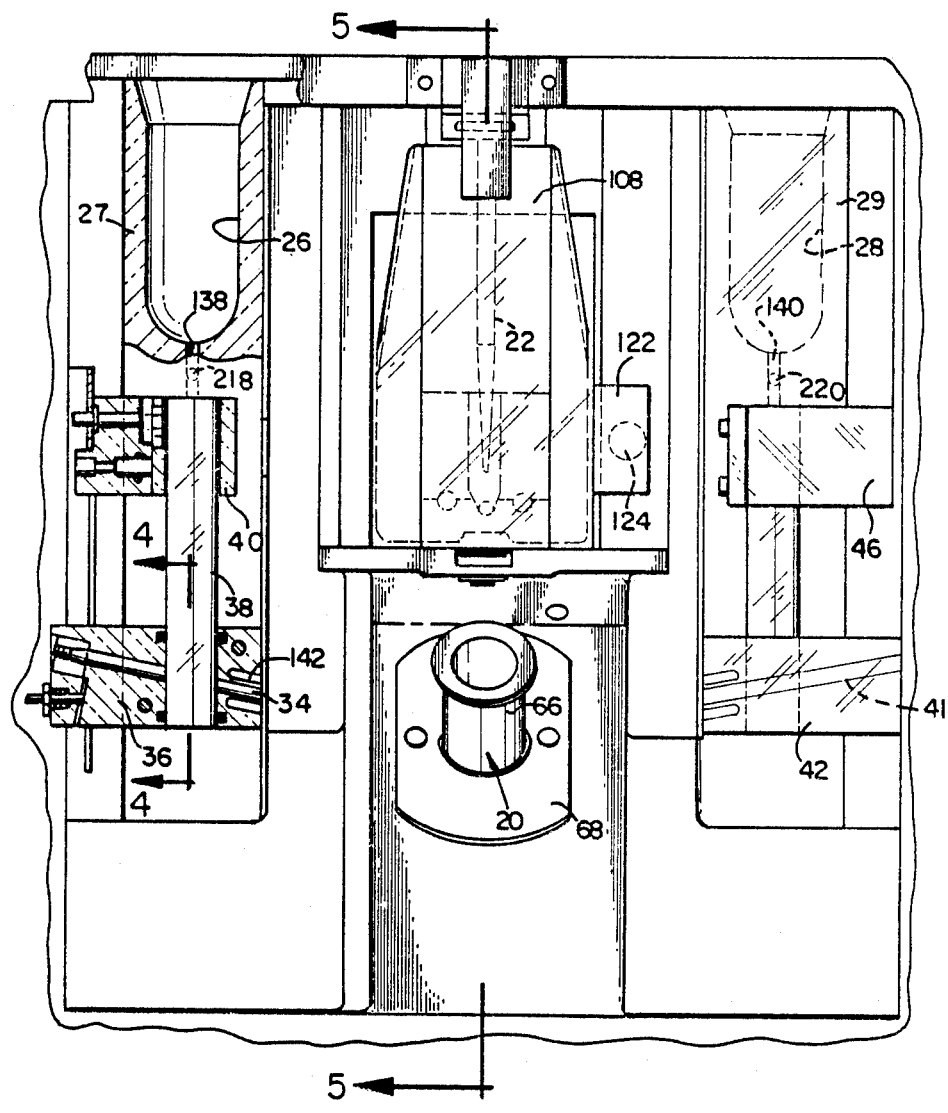
FIG. 3 is an enlarged view in somewhat more detail than FIG. 1, showing the blood sample handling apparatus.
Figure 7:
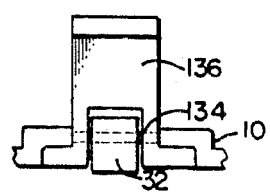
FIG. 7 is an enlarged detail of a start switch lever located beneath the upper cover of the device seen in FIG. 1.
Figure 5:
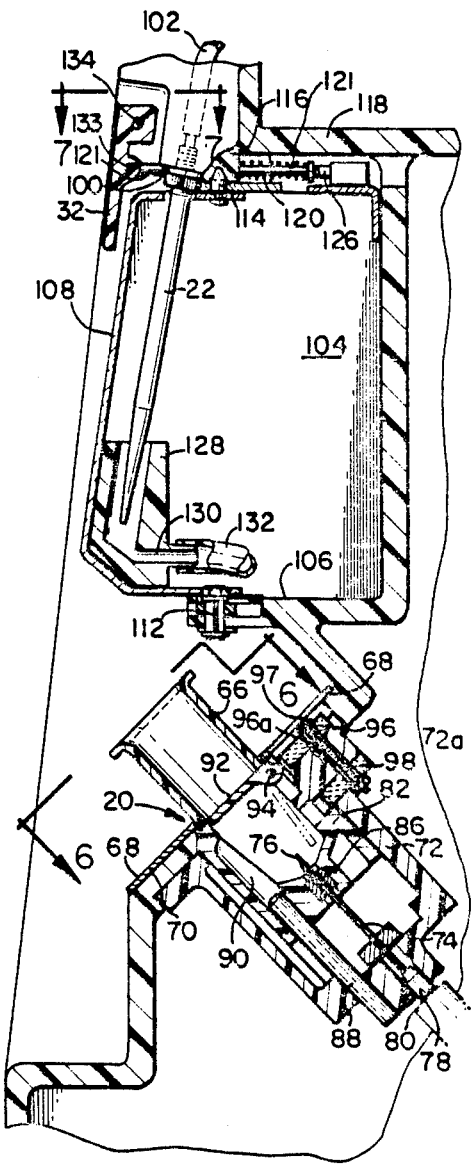
FIG. 5 is a sectional view taken along line 5—5 of FIG. 3.

FIG. 3 shows the start switch lever 32 with its associated support structure, which is also seen in greater detail in FIG. 7. In FIG. 7, lever 32 is shown to be pivotally supported by pin 134 on a bracket 136 mounted to a portion of the housing 30 below alcove. As seen in FIG. 5, lever 32 also has a second pin 133 by which it is pivotally connected to actuator rod 121. Rod 121 is urged by spring 120 into a switch 126, the spring loaded actuator of which is normally open. Therefore, when lever 32 is pressed and pivots about pin 134, it pushes pin 121 toward switch 126 allowing it to change state, if only briefly until the lever is released. The change in state of switch 126, however, can be used as one input to enable and set up for a processing sequence in the apparatus shown.

The nature of the blood sample inputs is better understood by reference to FIGS. 3 and 5.

It has become common to employ containers known as "vacutainers" which are containers sealed with a resilient stopper or closure and pre-evacuated to aid in the withdrawal of a specimen of blood from a person giving a blood sample. In prior art systems, no convenient way for handling such containers has been available and the present system does provide such an arrangement. The system is adapted specifically for a generally cylindrical bottle or test-tube-like structure with a resilient cap which may be punctured, for example, by a hypodermic needle. In accordance with the present invention, a receptacle and device 20 for introducing blood from vacutainers into the system provides a tubular guide 66 to guide the vacutainer into the apparatus. Guide 66 is terminated by an outwardly flanged collar at its opening. Surrounding the tubular guide 66 is a flange plate 68 removably mounted on a bevelled face 70 of the housing to close the opening, in the housing and act as a stop as will be described. A vacutainer is inserted within the guide 66, stopper or resilient closure down, at an angle, as seen in FIG. 5. Fixed to the housing beneath the bevelled face in general axially alignment with the guide 66, is a cup-shaped portion 72 of the frame structure which may be of any selected uniform cross-section. Cup-shaped frame member 72 is primarily a guide which, in other embodiments, is not necessarily a cup, but preferaby is a cup which provides a cylindrica interior guide surface. The cup-shaped frame member 72 supports on its bottom in generally axial position a penetrating tubular means, such as a hypodermic needle 74, having a sharpened end 76 designed to penetrate the resilient closure of a vacutainer. An interfitting coupling 78 connecting the removable hypodermic needle 74 and tubing 80 may be actually molded into the bottom of the cup 72. Guided within the cup guide 72, in sliding engagement therewith, is movable support means for the vacutainer in the form of a second cup member 82. Cup movable support means 82 provides movable support for the vacutainer in alignment with the needle 74. The guide means 66 is aligned with, fixed to and moves with cup member 82. The good sliding relationship of the support means 82 within the frame cup 72 enables reciprocating movement of the support means cup 82 axially up and down within the frame cup support 72.

The movable support cup 82 is shown in its upper position where it is stopped against the flange 68 which limits its outward movement. In this position, just the sharpened end 76 of the hypodermic needle 74 extends axially through the bottom of the support cup 82, preferably through suitable bearing means 86. Bearing 86 adds support to the penetrating hypodermic needle against lateral movement or bending near its tip and yet allows the inward pushing of a sealed container to move the movable cup 82 inwardly exposing more and more of the hypodermic needle to penetrate further in through the resilient self-sealing closure of the vacutainer. It should also be noted that the inner walls of movable cup 82 are tapered downwardly toward the center so as to tend to center the inserted vacutainer.

Also supported in the bottom of the frame cup 72 and penetrating the bottom of the movable support cup 82 in a direction parallel to cup movement is a vacuum drain tube 88. In preferred embodiments, therefore as the guide means cup 82 moves downward, the drain tube 88, like the hypodermic needle 74, stays in position. However, the drain tube 88 is located in an alcove 90 along the sidewall of the guide means so as to never constitute an obstacle to a vacutainer inserted in the cup 82. The position of this alcove is conveniently along the lowest portion of the tubular sidewall of cup 82 to constitute natural gutter or drain into the evacuation tube 88. Drain tube 88 is connected to a vacuum source at an appropriate time when the movable cup 82 is in its upper position to draw off fluids inside the cup.

Pivotally supported on the sidewall of the cup support means 82, just below the guide tube 66, is a closure flap 92. Flap 92 is preferably spring loaded by a tortion spring on the pin 94 to urge the flap into the position shown in FIG. 5 held against the bottom edge of guide tube 66 which is affixed to and moves with guide cup 82. The tortion spring, however, yields under the pressure of an inserted vacutainer to move into the position shown in phantom in FIG. 5 and allow the full insertion of the vacutainer.

Figure 6:
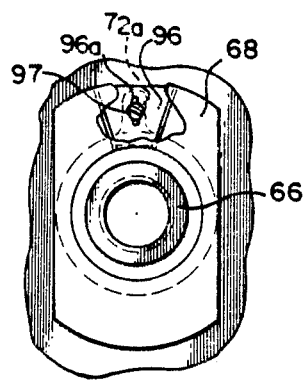
FIG. 6 is an axial view looking down in the vacuum container receptacle in the lower center portion of FIG. 3.

Also mounted along the sidewall of the frame cup 72 are a pair of photosensors, designated 96 and 98, which could be other types of sensing means, whether mechanical or electrical or optical. As seen in FIG. 6, the photosensors are advantageously wedge shaped in form. They are held in place by an insulated bolt 97 extending through holes corresponding to hole 96a in sensor 96 and through a hole in the intermediate separator bracket stub 76a molded integrally with cup 72.

Sensor 96 detects when a vacutainer is inserted as the flap 92 is displaced by a designed change in reflectance of light from the portion of the flap opposite it into sensor 96. If a highly reflective area, for example, is provided when the flap is displaced into the phantom position, that same reflectance will be detected by photocell 98 when the cup guide means has been fully depressed so that presumably the penetrating tubular means 74 has penetrated the resilient self-sealing closure. The signals from photocells 96 and 98 may be used to activate the rotary valve 24 to the proper position for receiving a blood sample from the vacutainer and for enabling syringe movement drawing blood from the container as described hereafter.

Similarly, when the vacutainer is withdrawn at the end of the processing, the return of the cup 82 to its initial position and the flap 92 to its closed position is detected by change in conditions sensed by the sensors 96 and 98. This, in turn, may enable an adjustment of the rotary valve and a reverse flush with the diluent from the syringe 50. This flush will clean out the protein from the hypodermic needle 74. The stream of diluent will be deflected by the flap 92, captured in the gutter 90 and evacuated by evacuation tube 88.

Withdrawal of the vacutainer is accomplished preferably by pulling on the outer flange of guide tube 66 to relieve the friction forces tending to pull the closure out of the vacutainer. The bottom of cup guide 82 holds the closure in place as it is withdrawn from the hypodermic needle.

Referring now to the aspirator structure, it will be observed in FIG. 5 that the aspirator tip 22 is supported on the housing by a suitable bracket 100 and connected by tubing 102 to the rotary valve 24 as schematically shown in FIG. 2. The aspirator tip 22 is supported to protrude downwardly and out of an alcove, generally designated 104, and beyond a bottom wall 106 of the alcove. The aspirator is thus positioned so that a beaker or other blood containing vessel can be held under it. The cover 108 is provided with spring means (not shown) which tends to move the cover into closed position shown in FIGS. 3 and 5 enclosing the aspirator tip 22. The cover is open to enable placement of a blood sample container under the aspirator tip 22. When the container is removed, the cover 108 can be manually returned about its pivot means to its closed position, as shown in FIG. 3, with the handle 122 resting against a surface of the housing providing a stop. Magnet 124 will attract magnet material of the handle to hold the cover closed. In this position, the aspirator tip is enclosed by cover 108 which has sidewalls in the form of a portion of truncated cone and generally parallel top and bottom semicircular walls closing the structure. The top and bottom walls provide means for its support and rotation. Rotation occurs about aligned pivot pins 112 and 114 fixed, respectively, in the bottom wall 106 and an extension 116 of top alcove wall 118, both part of the housing or frame. Also sensor means is preferably positioned to detect closed condition of the cover to activate the rotary valve to provide cleaning fluid to the aspirator tip 22. When the cover 108 is fully open a syringe in the system through the rotary valve will draw blood from the container 23 through the aspirator 22 and tube 102 into the rotary valve.

After the container is removed, and presumably the outside of the aspirator tip wiped clean, the closure can be moved by the handle to closed position, shown in FIGS. 5 and 3, wherein diluent from syringe 50 is forced through the aspirator to clean it. The cover 108 supports a recessed block 128 which encloses the aspirator tip 22 and provides a liquid collecting basin which directs the cleansing solution into a drain tube 130 connected to a hose 132 at the bottom. As shown in FIG. 2 the waste hose 132 is drained through valve Y16 to the internal waste 58.

As seen in FIG. 3, on the opposite sides of the intake are the red blood cell receptacle 26 and the white blood cell receptacle 28. These containers in the system are designed to be filled automatically and simultaneously. It is possible, however, for containers 26 and/or 28 to be filled manually with properly diluted solutions of a given sample. Instead of processing the whole series of tests automatically, in such case, the processing may be limited to the red or the white, depending upon whether one, or both containers, are used and the process can pick up from the point of filling those containers. Alternatively, the system in some embodiments can take a manual dilution for a white cell count, and automatically draw off and perform the further dilution for a red blood count. In order to fill either of the receptacles 26 and 28, the cover 130 shown in FIG. 1 must be raised. Blood samples properly diluted may then be placed in container 26 or container 28, or both.

Figure 4:
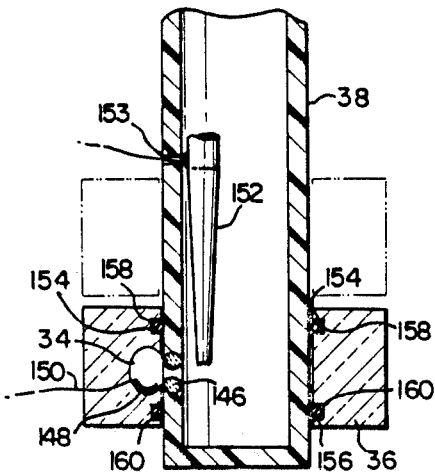
FIG. 4 is an enlarged detailed sectional view taken along line 4—4 of FIG. 3.

Whether filled automatically or manually, the blood collected in containers 26 or 28 is then processes through passage of 138 or 140 in the bottom of the container. Advantageously, containers 26 and 28 are formed in clear, transparent blocks through which passage 138 and 140 are bored. Passage 138 is, in turn, connected to a tubular passage 34 in block 36 by means of a hose which connects conveniently to coupling 142 in the block. Similarly, passage 140 connects to a similar hose connection to passage 41 in block 42. Passage 34 is arranged to pass tangentially by the jewel orifice 146 pressed into the tube 38. Orifice 146 is schematically represented in FIG. 2 and an orifice 148 for the white blood cell processing is similarly represented in FIG. 2. As seen in FIG. 4, on opposite sides of the orifice 146 are electrodes used in the pulse counting technique conventionally used in blood counting apparatus and broadly described, for example, in U.S. Pat. No. 3,921,066 of Angel Engineering Corporation. Specifically in passage 34, there is provided an electrode 148 which is placed along the periphery of the bore 34 and connected by suitable electrical connection 150 to a source of potential and the counting circuit. The electrode 148 is preferably a black platinum electrode electro-deposited on platinum. Inside tube 38 of insulating material, a larger tapered electrode 152 of fairly low impedance material is supported with its narrow end in proximity to the jewel orifice 146. Electrode 152 is connected by a suitable electrical lead at its larger remote end into the counting circuit. The taper of the electrode 152 is designed so that impedance decreases as cross-sectional area increases so that there can be an impedance balance between charges which reach the electrode 152 at the narrow end and those which reach it at the wider end. Those that reach the narrow end pass through a shorter, relatively lower impedance electrolite path, but then pass through a higher impedance path through the electrode. On the other hand, those that reach the broader lower impedance part of the electrode 152 must pass through a longer, higher impedance electrolite path. Thus, signal variations occurring in the prior art due to varying distances of travel to the electrode through the electrolite are compensated.

The present invention also provides that the block 36 may be moved relative to the insulating tube 38 from the position shown in solid lines to the position shown in phantom. Movement in this manner is facilitated by a sealing of the block 36 to the tube 38 using O-rings 154 and 156 in circumferential channels 158 and 160. Thus, the block is able to be moved up into the position shown in phantom in order to permit cleaning of the jewel orifice 146 and then returned to its active position wherein the passage 34 passes the orifice tangent to insulating tube 38 to permit flow through the orifice. In this particular version of the invention employing a transparent block, it is easy to visually aid repositioning of the block in proper position. When in active position shown in full lines in FIG. 4, any leakage which might otherwise possibly occur around the surface possibly between the sliding surfaces of the block 36 and the tube 38 is prevented by the O-rings 154 and 156 in channels 158 and 160.

It will be understood that the white blood cell count structure employing insulating tube 44 surrounded by block 42 containing passage 41 is similar to the red blood cell count structure except that orifice size is different and appropriate to the cells being counted.

Figure 8:
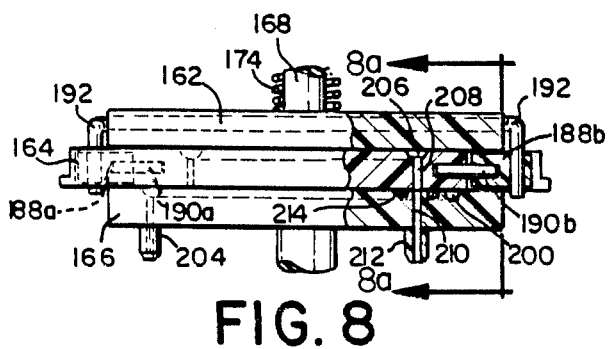
FIG. 8 is an enlarged side view similar to that of FIG. 1 partially in section of the rotary mixing valve of the present invention.
Figure 9:
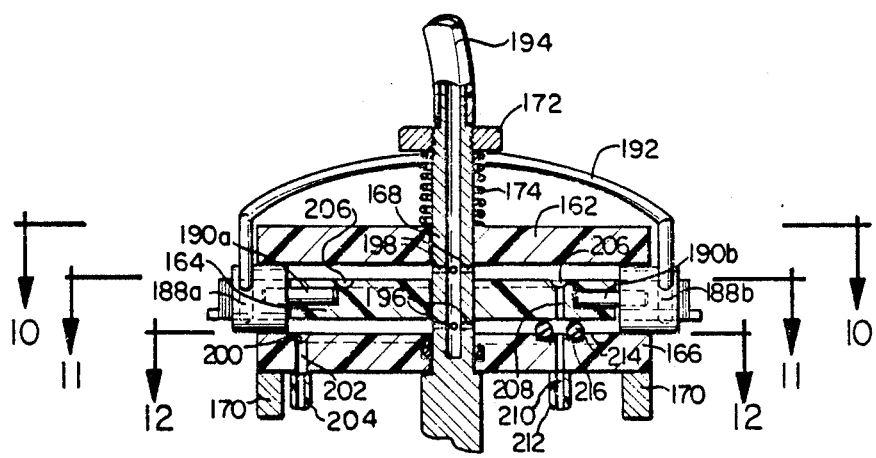
FIG. 9 is a sectional view of the rotary valve in open position for cleaning.
Figure 10:
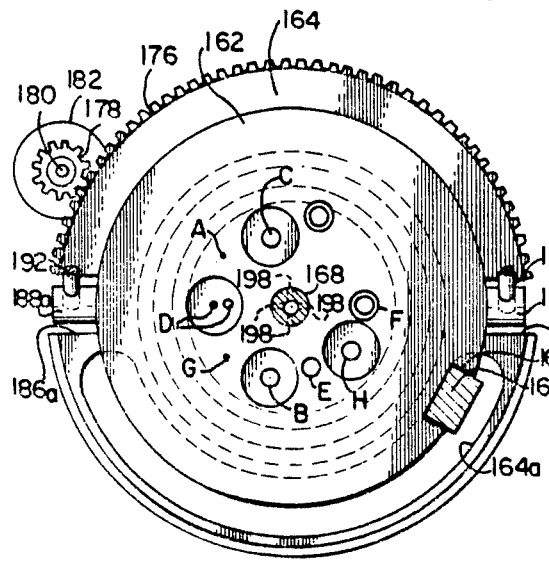
FIG. 10 is a sectional view along line 10—10 of FIG. 9.
Figure 11:
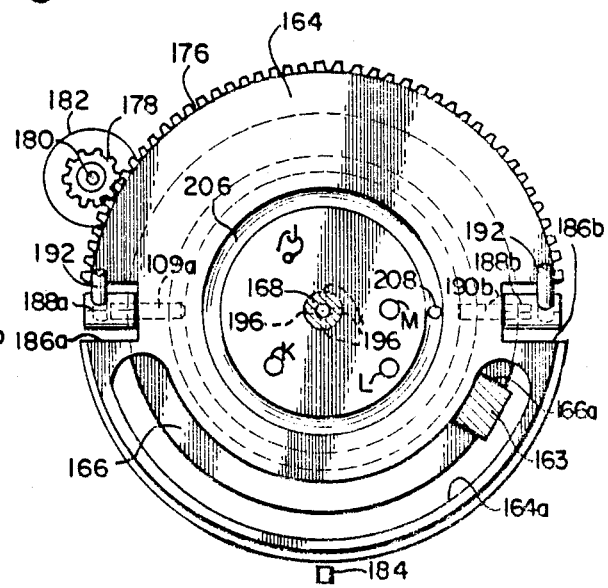
FIG. 11 is a sectional view along line 11—11 of FIG. 9.
Figure 12:
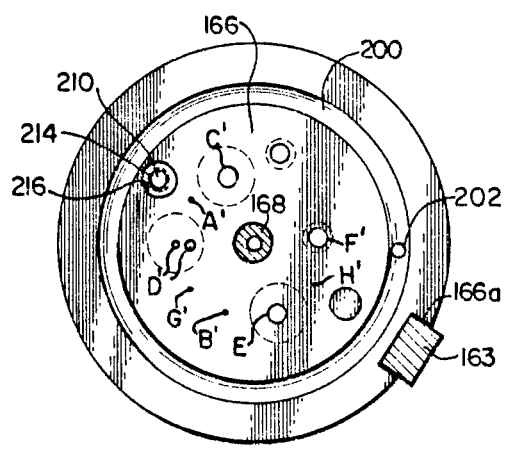
FIG. 12 is a sectional view along line 12—12 of FIG. 9.

Now considering the rotary valve 24 seen in FIG. 1, and illustrated in greater detail in FIGS. 8, 9 10, 11 and 12, it will be appreciated that the valve is composed of three cylindrical blocks 162, 164 and 166, sometimes called discs, with the middle block or disc 164 rotatable about the spindle 168. FIGS. 8 and 9 omit the input and output ports except for those relating to the vacuum system to be discussed, but it will be understood as clearly seen in FIGS. 10, 11 and 12, that each of the discs has ports through it. The ports in discs 162 and 166 seen in FIGS. 10 and 12 are located in positions essentially corresponding to one another. Thus, they are axially aligned at all times. However, the ports in movable disc 164 are moved from one position to another in order to effect different combinations of connections as illustrated in FIGS. 13a, 13b, 13c and 13d to be discussed hereafter. In the embodiment illustrated, the bottom disc 166 is supported on a pair of parallel rails 170 on the top of a horizontal wall within alcove 172 in housing 10. Alcove 172 is covered by transparent cover 30, which is ordinarily closed, as previously discussed. The spindle 168 is preferably supported on the housing structure to extend vertically upward and its top end is threaded to receive a retaining nut 172 which holds in place against the top disc 162 a compression spring 174. That compression spring 174 urges the discs together and into the parallel rails 170 supporting bottom disc 166. The top disc 162 and the bottom disc 166 are of somewhat smaller diameter and have similar keyways 162a and 166a provided in their peripheries. Those keyways accept a rectangular key post 163 or guide which permits vertical movement parallel to the spindle 168 but prevents rotational movement of the discs 162 and 166 since the key post is, in turn, affixed to the housing. Middle disc 164 is provided with an arcuate slot 164a permitting passage of key post 163 and allowing disc 164 to rotate a limited amount about spindle 168 sufficient to position disc 164 in each of three or four required positions for accomplishing the purposes of the rotary valve. Disc 164 is also provided with a segment gear means 176 which meshes with a pinion 178 on shaft 180 of vertically mounted motor 182. The motor 182, in turn, is supported on the housing at a fixed position relative to rotary valve 24 in order to drive the movable disc 164 of the rotary valve. Preferably a sensing means 184 is provided at the periphery of the rotatable member 164, as shown in FIG. 11 to sense calibrations on the disc 164 and therefore the position of disc 164 relative to the others in order to permit the stopping of the rotation at the proper alignment of ports.

Figure 8A:
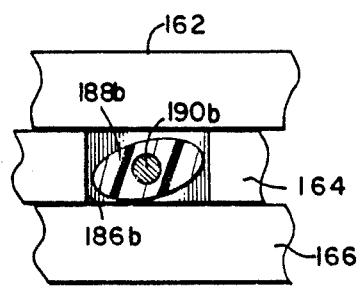
FIG. 8a is an enlarged view partially in section taken along line 8a—8a of FIG. 8.
Figure 8B:
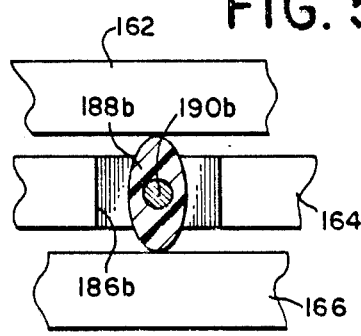
FIG. 8b shows the structure for FIG. 8a in alternate position.

The diametrically opposite edges of disc 164 are cut out to provide generally rectangular slots 186a and 186b within which are eccentric cam members 188a and 188b on stub shafts 190a and 190b directed along the diameter of the disc. Also attached to and mechanically connecting the eccentric cams 188a and 188b is a bail member 192 which allows simultaneous rotation of the cam members from a position shown in FIG. 8a to a position shown in FIG. 8b. The identical cams are centered in disc 164 and symmetrical about shafts 190a and 190b and so designed that working against the pressure of spring 174 they will separate upper disc 162 and lower disc 166 equal distances from disc 164. The spacing achieved by this action is intentionally kept very small, on the order of 0.005 to 0.010 inches between each of the discs.

Preferably, the spindle 168 at least at its upper end is a tube provided with a hose 194 connecting it to a supply of cleaning solution to clean the surfaces between the discs. Four ports 196, 90 degrees apart, are provided in position to line up with the spacing between discs 164 and 166 in the open position shown in FIG. 9. Another four ports 198, 90 degrees apart, are provided to line up with the spacing between discs 162 and 164 in the open position shown in FIG. 9. Rotation of the cams 188a and 188b to the positions shown in FIG. 8b will separate the discs a precise amount allowing the four radial orificea 196 between discs 168 and 164 to irrigate that area and the orifices 198 between the discs 164 and 162 to irrigate that area.

Also involved in the cleaning operation is a ring groove gutter in the top of disc 166 around all of the ports in that disc. Gutter 200 is provided with a vertical port 202 within the gutter and connected to the vacuum line 204 shown in FIG. 9. Gutter 200 functions to cause the vacuum to be distributed around the disc 166 so that it is effective in the very narrow space between the discs 164 and 162 and to draw the water in a sheet over the entire 360° circumference of each of those discs. The effect is to wash the entire top surface of disc 166 within the ring 200 and to wash the entire bottom surface of disc 164 out to the ring.

Similarly, a circumferential groove gutter 206 is provided in disc 164 at a radius smaller than the radius of the groove 200 but still outside of the ports in both disc 164 and 162. Groove 206 is connected by a vacuum line parallel to the axis extending through to disc 166. This is extended by port 210 through disc 166 to the vacuum line 212. Surrounding port 210 at the surface of disc 166 adjacent disc 164 is a small groove 216 which contains an O-ring 214. As best seen in FIG. 9, O-ring 214 is of such dimension that with the discs 166 and 164 at the maximum separation and in proper orientation to align the vacuum ducts 208 and 210, it will seal the space between those ducts to allow vaccum to be applied past the gap and to groove 206.

The valve as an operating structure is preferably formed of ceramic pieces having their opposing faces so highly ground and polished that they provide a molecular bond to one another when placed together. Such a surface is difficult to pull apart and difficult for fluids to move between, but it does permit relatively easy relative movement by sliding one surface over another, as occurs in the rotation of the valve of the present invention. The upper and the lower discs 162 and 166 are provided with similar ports. Disc 162, as seen in FIG. 10, has ports labeled A through H. Similarly, disc 166, as seen in FIG. 12, has ports A' through H' in the same relative positions so that as aligned by key post 163, correspondingly lettered ports of disc 166 will be axially aligned with those of disc 162. The middle movable disc 164, however, has a different pattern of ports J through M which cooperate with the aligned ports in the other discs to perform different functions in the different positions of disc 164. In general, the ports in the middle disc have been somewhat larger in diameter than those in the outer discs. Additionally, each of the discs has double ports D, J and D', which, at least in one situation (FIG. 13b), are aligned. The two ports in disc 164 are together called J, but the smaller of the two is the one which performs the blood sample measuring function for red blood cell analysis, and only that smaller port is filled with blood sample. Both the smaller port of double port J and the single white cell test port K are intended for measurements of highly repeatable volumes.

The ports J and K need not be precision formed since they may be calibrated in the equipment, but they must be stable in volume and not be subject to change in the normal use of the valve. The larger single hole is used in the white blood cell count since the amount of dilution required in the white blood count is relatively smaller than in the red blood count. In connection with the red blood count, the smaller of the pair of holes marked J is the one which is filled with the sample and then, in order to provide in a reasonable period of time the selected amount of diluent required for the red blood count, the larger parallel hole is provided. Thereby, while the sample is being washed out of the small hole by some of the diluent, an additional greater volume of diluent will pass through the larger hole, thereby enabling enough to pass through the valve 24 in the limited test time allowed for that valve position.

The various indexed valve positions assumed in operation have been shown highly diagramatically in FIGS. 13a, 13b, 13c and 13d. It will be understood that in these diagrams, only those lines connecting the operative ports in a given position have been shown for clarity. Also, the port locations are not intended to correspond to actual positions shown in FIGS. 10, 11 and 12.

Figure 13A:
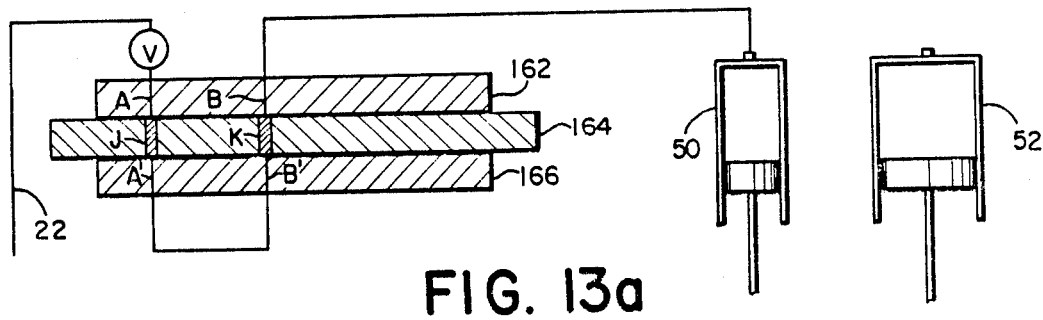
FIGS. 13a, 13b, 13c and 13d are sequential schematic views intended to show fluid flow paths through the rotary valve in successive positions.

FIG. 13a shows the rotary valve position in which aspiration is occurring and the metering holes K and the smaller of the pair J, are filled in series. This is accomplished by connecting the aspirator tip 22 in series through ports A, J, A', B', K, B and into the syringe 50 as the plunger of that syringe 50 is withdrawn to draw the blood sample toward it.

Figure 13B:
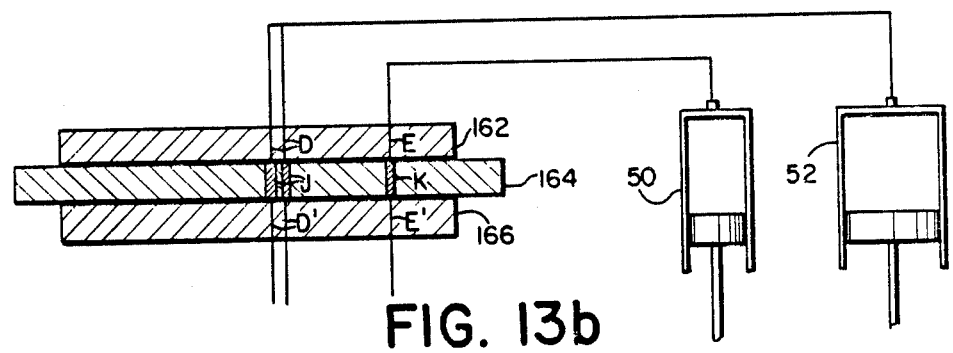

FIG. 13b shows the valve position for dilution wherein the larger syringe 52 filled with diluent is emptied through both of the ports J in parallel, the smaller port containing the blood and the larger port without blood. The double ports J are in series with the corresponding double ports D and D' in discs 162 and 166. Referring to FIG. 2, the larger syringe 52 empties through the double ports, including the smaller port containing the small measured blood sample into the red blood count container 26. At the same time, the smaller syringe 50 empties through the port K filled with a larger measured quantity of blood, entering through port E and exiting port E' to place the mixture in the red blood cell count container 26.

Figure 13C:
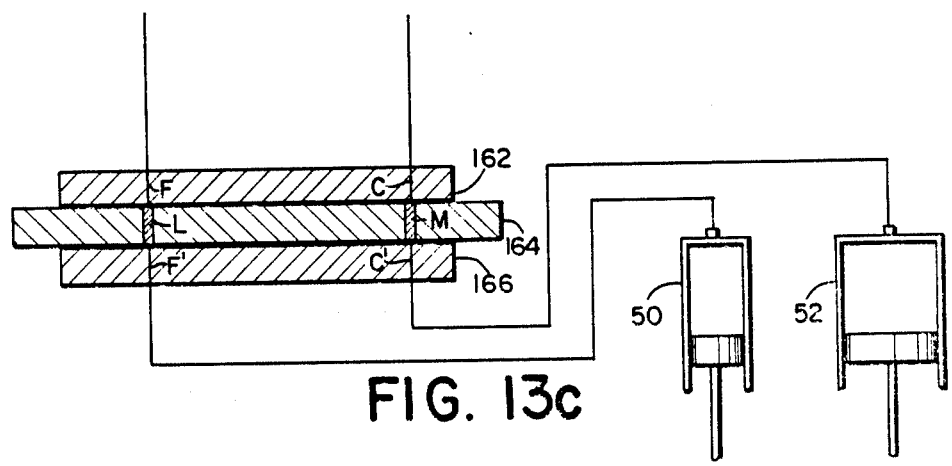

FIG. 13c shows the rotary valve position in which the syringes 50 and 52 are charged from the diluent supply 48. This is done bringing a line through ports F, L and F' to syringe 50 and through ports C, M and C' to syringe 52.

Figure 13D:
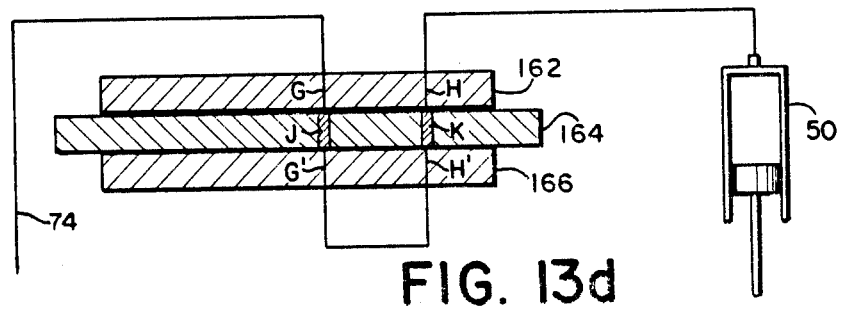

FIG. 13d is the alternative position to the valve for aspirating blood from a vacutainer source. As in FIG. 13a, only the smaller of the J ports in disc 64 is filled in series with the larger K port in disc 64 by drawing fluid into syringe 50. This occurs in series through port G, smaller port J, port G', then, back through port H', red cell metering port K and port H to syringe 50.

While the valve 24 herein has been shown and described as a particular type of rotary valve, it will be clear to those skilled in the art that many changes can be made in the rotary valve as shown. For example, making the two outer discs rotatable and the middle disc stationary will yield precisely the same results, although with greater complication. Other types of means of achieving separation of the discs such, for example, as some sort of wedge members engaged in the middle disc and wedging the outer discs away from the middle disc might be used alternatively, and many other mechanical systems for accomplishing this novel purpose will occur to those skilled in the art.

Also, the washing between the discs need not be confined to the system shown. Washing can be accomplished across the surfaces of the discs from the outside to the inside in another embodiment or need not be done in a radial direction at all. If the geometry shown is used, the number of ports at each location of the spindle can be varied and their direction need not be radial. Similarly, the vacuum drain gutters may be of a different shape and a different configuration and still be operable. The arrangement shown is preferred and believed to be most convenient, but it is understood that many operable variations will occur to those skilled in the art.

Also, the rotational geometry is a matter of preference and choice, but other types of relative motion and geometry can be employed. For example, it will be apparent to those skilled in the art that a lateral motion, not necessarily, but preferably rectilinear, and preferably continuously in line, could also be used. In such a variation, it would undoubtedly be advantageous to make the discs rectangular solid blocks to facilitate their relative linear movement. The use of polished ceramic to achieve a surface molecular bond is preferred, but other materials could be used. Again, movement of the middle block relative to the outside blocks is preferred, but conceivably movement of the outside blocks relative to the middle block would also be possible. It is also possible in this day of computer controls to have a complex movement in which all three blocks move relative to one another to different indexed positions to align ports in different configurations and the blocks might move in linear or curved paths between indexed positions. In fact, the paths need not be aligned or following a continuous curve and, indeed, individual blocks might move in different directions at the same time.

If a rectilinear or other geometry were selected, it would still be advantageous and important to employ the novel separation means for cleaning and preferably ports permitting cleaning fluid to be directed between the blocks and some sort of vacuum gutter arrangement to contain the cleaning fluid within the valve.

Referring now to FIG. 2, the overall operation of the system will now be described. It will be appreciated by those skilled in the art that the apparatus described thus far enables automation of the system wherein the devices described, plus other devices and mechanisms shown schematically in FIG. 2, are automatically controlled by the computer contained within housing 10 using the input controls 16, seen in FIG. 1.

To begin the process, diluent is drawn from supply 48 by opening solenoid valve v17. In order to know the amount of diluent drawn into or dispensed, sensors 234 and 236 are mounted on the housing of the syringes 50 and 52, respectively, in each case to determine a "home" reference position and to enable digital counting of predetermined volume units of diluent drawn into or dispensed from the syringe in response to controlled rotation of a drive motor. After positioning rotary valve in the position shown in FIG. 13c, diluent fluid is then drawn into the syringes to essentially fill them. As a practical matter, the syringes are motor driven. Drive is preferably done positively, such as by providing a rack gear along the plunger handle of such syringe. A pinion gear 238 may be driven in either direction by motor 240 to move the plunger of syringe 50 upon command. A pinion gear 242 is similarly driven by motor 244 to move the plunger of larger syringe 52.

With diluent in the syringes, the apparatus is ready to work and a blood sample may be drawn through the aspirator tip 22 from an open container by repositioning the rotary valve 24 to the position of FIG. 13a or from a vacuum container by repositioning the rotary valve to the position of FIG. 13d upon inserting the vacutainer into receptacle 20. In order to aspirate, vacuum is drawn by further withdrawal of the plunger of syringe 50, as illustrated in FIGS. 13a or 13d. Either way, a sample is drawn into the smaller measuring bore of the pair of bores J and the large measuring bore K in disc 164. The sample is retained within those bores as the disc 164 is rotated to the position of FIG. 13b. A measured amount of diluent from syringe 50 is fed through bore K to wash out the measured volume of blood sample in the larger hole into the white blood count container 28 and provide sufficient diluent for the white blood cell test. At the same time, the measured proper amount of diluent from syringe 52 is fed through both of the two bores J to wash out the measured volume of blood sample therein and mix it with the proper amount of diluent in the red blood count container 26. At this point, the normally closed valve V14 is opened for a very short measured time, on the order of one and a half second, to add the required amount of lyse from container 54 to disolve the hemoglobin. This occurs under pressure applied from pump 56.

valves V3 and V9 which, like many of the valves of the system, are preferably pinch valve members located to pinch rubber hose portions of the line along which they are interposed. Opening normally closed valve V3 draws red blood count mixture into tube 34 (FIGS. 4 and 3) past jewel orifice 146 due to the presence of a vacuum in an internal waste tank 58. Similarly, opening normally closed valve V9 draws white blood count mixture from container 28 through the tube 40 past jewel orifice 148 due to the presence of the vacuum in internal waste chamber 58.

After samples have been moved into the lines respectively passing jewel orifice 146 and 148 by opening valves V3 and V9, valve V5 is then opened briefly to interject an air bubble from 218 and 220 into each of the lines 138' and 140' from each of the red and white blood counting chambers 26 and 28. This opening is for a very short period, just long enough for air from pump 56 to form a discontinuity in the blood sample. valves V3 and V9 are then closed and valves V11 and V12 are opened to draw the respective blood samples through jewel orifices 146 and 148, respectively, due to the vacuum in the internal waste tank 58. The bubble interposed in the line forms a visible, or otherwise sensible, discontinuity, which may be sensed as it passes a sensor along or in the line. Passage of the bubble between two sensing points along lines 138' or 140' represents the passage of an equivalent volume of the blood sample through the orifice to fluid volume contained in that line between the sensing points. Transparent tubing 138' may be employed between the red blood container 26 and the jewel 146, and similar transparent tubing 140' between white blood container 128 and jewel 148.

In practice, it is preferred to use clear plastic blocks 27 and 29 and extend the bores 138 and 140 beneath containers 26 and 28 as seen in FIG. 3. In such event, the blocks are extended down to the level of blocks 36 and 42. Air bubble injection ports for lines 218 and 220 are then conveniently placed just below containers 26 and 28 as seen in FIG. 3. Photosensors (not shown) located in blocks 27 and 29 along the lines 138 and 140 can then sense the discontinuity between the liquid and the bubble in bore 138 and 140 to produce a pulse or step signal.

Such photosensors as seen in FIG. 2 are placed at the beginning and end of a measured length of the respective lines 138' and 140'. Discontinuities in the lines are sensed to respectively start and terminate the count of the counter, thus, applying the count to a known measured volume in each case. Sensors 222 along line 138 initiate such counting for the red blood count, and sensors 224 along line 140 initiate the counting for the white blood count. Sensors 226 along line 138 terminate the red blood count and sensors 228 along line 140 terminate the white blood count.

In the course of such counting, an HGB measurement is made using the HGB detector 230 in a line parallel to the line containing valve V9 by opening valve V10, and perhaps closing valve V9 briefly in the process.

Also, just before counting begins on the red blood count side, valve V17 is opened together with valve V15 and valve V11 to waste 58 to supply diluent which is advantageously also an electrolyte solution at a high rate to sweep away cells from the back or internal side of jewel orifice 146. During counting, valve V15 is closed but valve V13 is opened to cause a reduced flow of cleaning diluent through choke 232 past jewel orifice 146 to sweep away platelets to avoid recounting of those small particles which oth ⒭rwise might produce error due to their swirl around electrode 152 in tube 38.

Once the count is completed, the sample can be fully evacuated from the container 26 and 28 by opening valves V3 and V9.

The rotary valve 24 is then placed in the position of FIG. 13b, and clean diluent is passed through the measuring orifices and into the red and white blood count containers 26 and 28 to rinse them. Then, containers 26 and 28 are evacuated through valves V3 and V9 to internal waste 58.

The system can be designed so that the tubes normally containing fluid are kept wet by arranging the timing of evacuation to occur just before the new sample is introduced.

The system of the present invention makes possible completely automatic cycling which can be programmed for computer control. Such programming enabling complete automation and rapid throughput through the device is made possible not only by the described features of the present invention but by the control system and software which are the subject of a separate disclosure.

Some variations in some of the components of the present invention are possible. Others will occur to those skilled in the art and devices not described in alternative form are also capable of modification. Moreover, the fluid system overall is capable of numerous variations. The claims contemplate such variations and modification, and all such variations and modifications within the scope of the claims are intended to be within the scope and spirit of the present invention.

We claim:

1. A valve comprising spindle means defining a centrally disposed flow through passageway with outwardly disposed ports, three stacked members centrally disposed on the spindle means and whose mating surfaces are rotatably slidable relative to one another, a middle one of which stacked members is movable relative to the other two, the middle member having at least two positions of operation wherein at least one port through the middle member is aligned with aligned ports in the outer two members, retaining means on each side of the stacked members fixed to the spindle means on opposite sides of the stacked members for confining the stacked members in the direction of stacking between the respective retaining means, means between at least one of the retaining means and the stacked members urging the stacked members together, and means acting to separate the stacked members from one another and position them such that the outwardly disposed ports will direct cleaning liquid flow between each pair of the separated members.

2. The rotary valve of claim 1 in which the spindle is fixed to a frame as part of the frame and the three stacked members have openings receiving the spindle, the means urging the stacked members together is a spring means, and the three stacked members and spring means are confined between the retaining means on the spindle, so that the spring means urges the stacked members together, and means is provided for acting between the stacked members against the force of the spring means to separate the members to allow cleaning liquid from the ports in the spindle to flow between each pair of separated members.

3. The rotary valve of claim 2 in which coupled eccentric cam means are rotatably supported on the middle member whereby when the cams are rotated the members are separated along the spindle by a controlled spacing.

4. The rotary valve of claim 3 in which the eccentric cam means are a pair of coaxial eccentric cams held in slots in the middle member on diametrically opposed and aligned shafts which extend into and are rotatably supported by the middle member and the rotatable members are connected by a common actuating bail, movement of which moves the cams simultaneously to separate the stacked members or to permit the stacked members to close together.

5. The rotary valve of claim 2 in which the spindle is hollow and connectable to a source of cleaning fluid and ports in the spindle are directed between the members when separated to enable washing of each of the opposed member surfaces.

6. The rotary valve of claim 5 in which each pair of adjacent members is provided with a gutter in one of the opposed member surfaces and surrounding the ports, and port means through at least the members containing the gutters connecting the respective gutters to drain systems.

7. The rotary valve of claim 6 in which the gutters are provided on the bottom member of each adjacent pair of stacked members and the port means to drain the gutter of the middle members passes through the middle member parallel to the axis of rotation and an aligned port in the bottom outside member and a compressible ring seal between the bottom and middle members is contained in a groove in the bottom member and arranged to compress when the members are closed together under normal spring pressure closing the members together and still maintain a seal against the middle member when the discs are separated for washing.

* * * * *

UNITED STATES PATENT AND TRADEMARK OFFICE
CERTIFICATE OF CORRECTION

PATENT NO. : 4,729,876

DATED : March 8, 1988

INVENTOR(S) : James W. Hennessy et al.

It is certified that error appears in the above-identified patent and that said Letters Patent is hereby corrected as shown below:

```
    Column 6, line 58, "cylindric" should read
--cylindrical--.
    Column 8, line 62, "Y16" should read --V16--.
    Column 11, lines 22-23, "orificea" should read
--orifices--.
    Column 14, line 41, "valves" should read --Valves--.
    Column 15, line 39, "oth®rwise" should read
--otherwise--.
```

Signed and Sealed this

Third Day of October, 1989

Attest:

DONALD J. QUIGG

Attesting Officer

Commissioner of Patents and Trademarks